United States Patent
Song et al.

(10) Patent No.: US 11,479,778 B2
(45) Date of Patent: Oct. 25, 2022

(54) **CONSTRUCTION OF ACCUMULATING *MUCOR CIRCINELLOIDES* STRAIN AND INDUSTRIAL APPLICATION OF CONSTRUCTED STRAIN**

(71) Applicant: SHANDONG UNIVERSITY OF TECHNOLOGY, Zibo (CN)

(72) Inventors: Yuanda Song, Zibo (CN); Caili Sun, Zibo (CN); Huaiyuan Zhang, Zibo (CN); Wu Yang, Zibo (CN); Meiling Chen, Zibo (CN)

(73) Assignee: SHANDONG UNIVERSITY OF TECHNOLOGY, Shandong (CN)

( * ) Notice: Subject to any disclaimer, the term of this patent is extended or adjusted under 35 U.S.C. 154(b) by 0 days.

(21) Appl. No.: 17/285,816

(22) PCT Filed: Nov. 30, 2020

(86) PCT No.: PCT/CN2020/132738
§ 371 (c)(1),
(2) Date: Apr. 15, 2021

(87) PCT Pub. No.: WO2021/238127
PCT Pub. Date: Dec. 2, 2021

(65) Prior Publication Data
US 2022/0186237 A1 Jun. 16, 2022

(30) Foreign Application Priority Data

May 26, 2020 (CN) .......................... 202010455770.0
Nov. 19, 2020 (CN) .......................... 202011299212.6

(51) Int. Cl.
*C12N 15/80* (2006.01)
*C12N 9/10* (2006.01)

(52) U.S. Cl.
CPC .......... *C12N 15/80* (2013.01); *C12N 9/1029* (2013.01); *C12Y 203/0102* (2013.01)

(58) Field of Classification Search
CPC . C12N 15/80; C12N 9/1029; C12Y 203/0102
See application file for complete search history.

(56) References Cited

FOREIGN PATENT DOCUMENTS

| CN | 101220334 A | 7/2008 |
|---|---|---|
| CN | 101445815 A | 6/2009 |
| CN | 103642859 A | 3/2014 |
| CN | 104099254 A | 10/2014 |
| CN | 104946539 A | 9/2015 |
| CN | 106635837 A | 5/2017 |
| CN | 107574190 A | 1/2018 |
| CN | 111575301 A | 8/2020 |

OTHER PUBLICATIONS

Cuomo et al., GenBank accession No. EPB86486, Mar. 2015.*
Xin Tang, "Molecular mechanism of high lipid-production in oleaginous fungus *Mucor circinelloides* WJ11," Doctorate Thesis, Jiangnan University (Jun. 15, 2016).
Yao Zhang et al, "Mucor circinelloides WJ11 lipase gene cloning, expression, and characterization," 1th China Enzyme Engineering Meeting Paper Collection, Aug. 11, 20219, p. 104.
Luning Zhang, "Indentification and functional analysis of acyl-CoA: diacylglycerol acyltransferase form oleaginous fungus *Mucor circinelloides*" Mater's Thesis, Jiangnan University (Dec. 15, 2015).
Nattapat Isarankura Na Ayudhya et al., "Metabolic traits specific for lipidoverproducing strain of Mucor circinelloides NJ11 identified by genome-scale modeling approach," Peer J. vol. 7, No. e7015, pp. 1-9 (Jul. 6, 2019).
Jian Cao, et al., "Comparison of several methods for extracting oil from Mucor circinelloides," China Oils and Fats, vol. 4, No. 29, pp. 38-40.

* cited by examiner

*Primary Examiner* — Delia M Ramirez
(74) *Attorney, Agent, or Firm* — SZDC Law P.C.

(57) ABSTRACT

The present invention relates to the technical field of gene engineering and particularly relates to a method for constructing non-de novo synthesized *Mucor circinelloides* recombinant strain with high lipid yield, recombinant strain constructed by method, and application of recombinant strain. According to the present invention, a diacylglycerol acyltransferase gene (DGAT) is overexpressed in *Mucor circinelloides* WJ11 by a homologous recombination technology, and exogenous oil is added for fermentation, such that the non-de novo synthesized *Mucor circinelloides* recombinant strain with high lipid yield is constructed. Compared with the control strain Mc2075, the fat yield of the *Mucor circinelloides* is increased; and when the diacylglycerol acyltransferase (DGAT) is transformed into the uracil defective type of *Mucor circinelloides* WJ11, the fatty acid composition changes after fermentation, and the lipid content may reach 53% of dry cell weight after the fermentation condition is optimized.

7 Claims, 2 Drawing Sheets
Specification includes a Sequence Listing.

CONSTRUCTION OF ACCUMULATING *MUCOR CIRCINELLOIDES* STRAIN AND INDUSTRIAL APPLICATION OF CONSTRUCTED STRAIN

This application is the National Stage Application of PCT/CN2020/132738, filed on Nov. 30, 2020, which claims priority to Chinese Patent Application Nos. 202011299212.6, filed on Nov. 19, 2020, and 202010455770.0, filed on May 26, 2020, both of which are incorporated by reference for all purposes as if fully set forth herein.

BACKGROUND OF THE INVENTION

1. Technical Field

The present invention belongs to the field of gene engineering and particularly relates to a method for constructing a non-de novo synthesized *Mucor circinelloides* recombinant strain with high lipid yield, the recombinant strain constructed by the method, and application of the recombinant strain. According to the present invention, a diacylglycerol acyltransferase gene (DGAT) is overexpressed in *Mucor circinelloides* WJ11 by a homologous recombination technology, and exogenous oil is added for fermentation, such that the non-de novo synthesized *Mucor circinelloides* recombinant strain with high lipid yield is constructed.

2. Description of Related Art

Microorganisms that can accumulate fat exceeding 20% of their dry weight are called oil-producing microorganisms, which are widely distributed, mainly including fungi, yeasts, bacteria and microalgae. Since the oil-producing fungus *Mucor circinelloides* is rich in γ-linolenic acid, people have studied it more and more deeply. The *Mucor circinelloides* is the first strain for industrially producing linolenic acid in the world. Since the *Mucor circinelloides* has high lipid-producing ability, the genome has been sequenced and the gene research system is perfect, the *Mucor circinelloides* serves as a model organism for studying production of the linoleic acid by the microorganisms.

Polyunsaturated fatty acids (PUFAs), which only can be obtained through diet, are essential fatty acids for human body and are very beneficial to human nutrition and health, so more and more people pay attention to the polyunsaturated fatty acids. Mammals (including human beings) can only synthesize saturated fatty acid (SAFA) and monounsaturated fatty acid (MUFA) in vivo, and ω-6 and ω-3 series polyunsaturated fatty acids such as linoleic acid (LA, 18:2, n-6) and α-linolenic acid (ALA, 18:3, n-3) cannot be synthesized in vivo. The linoleic acid and the linolenic acid may be used to synthesize docosapentaenoic acid (DPA, 22:5, n-6) and docosahexaenoic acid (DHA, 22:5, n-3) after being catalyzed by various enzymes. Studies have found that obesity, hypertension, diabetes, coronary arteriosclerosis, schizophrenia, senile dementia and the like are related to the metabolism of essential fatty acids. Therefore, the essential fatty acids and the derivatives thereof are of great significance for human health.

Studies have shown that the diacylglycerol acyltransferase (DGAT) is the key enzyme in the synthetic route of triacylglycerol, is the enzyme required for the final step in the synthesis of the triacylglycerol, and can catalyze the conversion of diacylglycerol into the triacylglycerol. There are two kinds of diacylglycerol acyltransferase (DGAT) in the mucor circinelloides, namely DGAT I and DGAT II, both of which are membrane-bound proteins. In recent years, there have been numerous studies on the *Mucor circinelloides* diacylglycerol acyltransferase (DGAT), mainly focusing on the effect in the fat synthesis route, but more studies have focused on the heterogeneous expression of the enzyme in other strains and have found that the lipid content of the strain expressing the enzyme is increased. However, there are few studies on the endogenous over-expression of the *Mucor circinelloides* diacylglycerol acyltransferase (DGAT) in the *Mucor circinelloides* to increase the lipid accumulation quantity.

BRIEF SUMMARY OF THE INVENTION

In view of the problems in the prior art, the preliminary study of the present invention found that in a strain of *Mucor circinelloides* with fat accumulation quantity capable of reaching 36%, γ-linolenic acid content in the intracellular fatty acid composition is 18-19%, and the fermentation condition has high controllability. Therefore, in the present invention, according to the advantageous conditions of the strain, the *Mucor circinelloides*-derived diacylglycerol acyltransferase (DGAT) is endogenously expressed in the *Mucor circinelloides* by a gene engineering method of homologous recombination, and a non-de novo synthesized *Mucor circinelloides* recombinant strain with high lipid yield is constructed, thereby providing guidance for vigorously promoting the industrial application of the *Mucor circinelloides*.

To achieve the above objective, the present invention adopts the following technical solutions:

According to a method for constructing a non-de novo synthesized *Mucor circinelloides* recombinant strain with high lipid yield, the nucleotide sequence of diacylglycerol acyltransferase DGAT is connected to integrative plasmid pMAT2075, the recombinant plasmid is electrically transformed into a protoplast of uracil defective *Mucor circinelloides*, and positive clones are screened, such that the diacylglycerol acyltransferase DGAT is overexpressed in the uracil defective *Mucor circinelloides* to obtain the non-de novo synthesized *Mucor circinelloides* recombinant strain with high lipid yield.

Based on the above solution, the nucleotide sequence of the diacylglycerol acyltransferase DGAT is as shown in SEQ ID NO: 1.

Based on the above solution, the uracil defective *Mucor circinelloides* is the uracil defective type of *Mucor circinelloides* WJ11.

In a non-de novo synthesized *Mucor circinelloides* recombinant strain with high lipid yield constructed by the above method, the *Mucor circinelloides* recombinant strain with high lipid yield is a *Mucor circinelloides* DGAT strain, which was preserved in China General Microbiological Culture Collection Center (CGMCC) on Sep. 23, 2020, and the preservation number of the strain is CGMCC No. 20730.

The non-de novo synthesized *Mucor circinelloides* recombinant strain with high lipid yield is applied to production of lipid through fermentation.

According to a method for producing lipid by the non-de novo synthesized *Mucor circinelloides* recombinant strain with high lipid yield through fermentation, a seed culture solution is inoculated on a fermentation medium added with fat as a carbon source according to the inoculation quantity of 10%, and a defoaming agent polypropylene glycol 2000 is added according to 2 mL/L during fermentation, wherein the fermentation conditions are 28° C. and 600 rpm, the air inflow is 1 v/v min$^{-1}$, and the pH is maintained to be 6.0.

Based on the above solution, the 1L of fermentation medium consists of: 40 g of glucose, 21.6 g of fat, 1.5 g of $MgSO_4 \cdot 7H_2O$, 100 μL of metal mother liquid, 2 g of ammonium tartrate, 7.0 g of $KH_2PO_4$, 2 g of $NaHPO_4$, 1.5 g of yeast extract, 0.1 g of $CaCl_2 \cdot 2\ H_2O$ and the balance of water, wherein the metal mother liquid consists of: 8 g of $FeCl_3 \cdot 6H_2O$, 1 g of $ZnSO_4 \cdot 7H_2O$, 0.1 g of $CuSO_4 \cdot 5H_2O$, 0.1 g of $Co(NO_3)_2 \cdot 6H_2O$, 0.1 g of $MnSO_4 \cdot 5H_2O$ and the balance of distilled water to prepare 100 mL.

Based on the above solution, the fat is soybean oil.

Based on the above solution, the fat is added after being emulsified, wherein the emulsification process is as follows: adding 1 wt % of tween 80 and a small amount of water into the fat, performing homogenization by a homogenizer for 5 min under the condition of 8000 rpm, performing ultrasonic treatment for 5 min and then performing homogenization for 3 min.

The technical solution of the present invention has the following advantages:

In the non-de novo synthesized *Mucor circinelloides* recombinant strain with high lipid yield constructed by the method provided by the present invention, the *Mucor circinelloides*-derived diacylglycerol acyltransferase (DGAT) is integrally expressed on the *Mucor circinelloides* genome, and compared with the control strain Mc2075, the fat yield of the *Mucor circinelloides* is increased; and when the diacylglycerol acyltransferase (DGAT) is transformed into the uracil defective type of *Mucor circinelloides* WJ11, the fatty acid composition changes after fermentation, and the lipid content may reach 53% of dry cell weight after the fermentation condition is optimized.

Most of the existing experiments for producing lipid through microbial fermentation are the de novo synthesis process taking glucose as a carbon source, and in this process, various enzymes and other substances are mobilized in the microorganisms to promote the synthesis of fatty acids. The glucose is degraded in the cytoplasm, and the specific reaction needs 10 steps. The de novo synthesis of the fatty acids needs multi-step reactions such as initiation, "condensation, reduction, dehydration and reduction", circulation and release. The main product is palmitic acid. The longer fatty acids are formed on the basis of the palmitic acid by extending the carbon unit.

According to the non-de novo synthesized *Mucor circinelloides* recombinant strain with high lipid yield constructed by the present invention, in the presence of exogenous oil, the cell uses the exogenous oil as the carbon source, the exogenous oil is degraded into micromolecular fatty acid by extracellular lipase, and after entering the cell, the free fatty acid directly participates in the synthesis process of intracellular lipid in the form of short fatty acid chain. Compared with the de novo synthesis of the lipid, this method greatly shortens the lipid synthesis time and improves the lipid accumulation efficiency. Furthermore, when lipid synthesis is performed by taking the fatty acid as a substrate, unsaturated fatty acid with higher degree of unsaturation may be obtained.

DETAILED DESCRIPTION OF THE INVENTION

Figure 1:
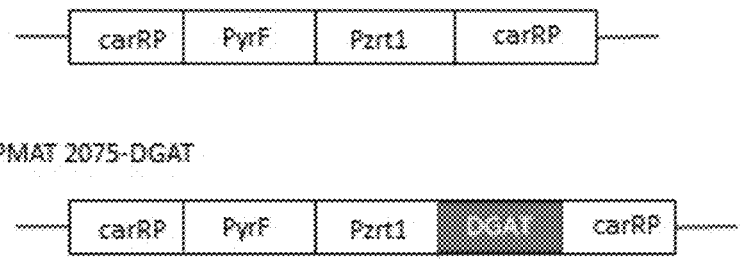
FIG. 1 is a *Mucor circinelloides* recombinant plasmid pMAT2075-DGAT diagram.

Terms used in the present invention, unless otherwise specified, generally have meanings commonly understood by those of ordinary skill in the art.

The present invention will be described in detail below in combination with the specific embodiments and with reference to data. The following embodiments are only intended to illustrate the present invention, rather than to limit the scope of the present invention in any way.

Embodiment 1

(1) Cloning of *Mucor circinelloides* diacylglycerol acyltransferase (DGAT)

*Mucor circinelloides* WJ11 was inoculated into a 500 mL conical flask with a baffle containing 100 mL of Kendrick culture medium (glucose: 30 g/L, $MgSO_4 \cdot 7H_2O$: 1.5 g/L, ammonium tartrate: 3.3 g/L, $KH_2PO_4$: 7.0 g/L, $Na_2HPO_4$: 2.0 g/L, yeast extract: 1.5 g/L, $CaCl_2 \cdot 2H_2O$: 0.01 g/L, $FeCl_3 \cdot 6H_2O$: 8 mg/L, $ZnSO_4 \cdot 7H_2O$: 1 mg/L, $CuSO_4 \cdot 5H_2O$: 0.1 mg/L, $Co(NO_3)_2 \cdot 6H_2O$: 0.1 mg/L, and $MnSO_4 \cdot 5H_2O$: 0.1 mg/L) for cultivation under the conditions of 28° C. and 150 rpm for 48 h, and thalluses were collected through suction filtration. The mRNA of the *Mucor circinelloides* strain was extracted and was reversely transcribed into cDNA, referring to the instruction of a reverse transcription kit. Diacylglycerol acyltransferase (DGAT) (K14457, 1086 bp) was found according to the genome information of the measured WJ11, specific primers DGAT-F and DGAT-R were designed according to the gene sequence, and PCR was conducted by taking the *Mucor circinelloides* cDNA obtained above as a template.

```
                                         (SEQ ID NO: 2)
DGAT-F: 5'-AGTCGCTAGCATGAACAGCTCTTCTGAGAC-3'

(SEQ ID NO: 3)
DGAT-R: 5'-AGTCGCTAGCTCAATCGGTGATACGCAGTT-3'
```

PCR reaction was conducted in a 50 μL system: 5×PS buffer 10 μL, dNTPs Mixture (each 2 mM) 5 μL, upstream primer 1 μL, downstream primer 1 μL, total cDNA 100-200 ng, PrimeSTAR HS DNA Polymerase 1 μL, and $ddH_2O$ supplemented to 50 μL.

The reaction conditions are as follows: after denaturation was conducted at 95° C. for 3 min, circulation started, denaturation was conducted at 95° C. for 30 sec, annealing was conducted at 55° C. for 30 sec, extension was conducted at 72° C. for 1.5 min, and after 30 cycles, extension was conducted at 72° C. for 10 min and the temperature was reduced to 4° C. kept for 5 min. A PCR fragment of 1265 bp was obtained through amplification, wherein the nucleotide sequence is as shown in SEQ ID NO: 1.

```
  1 atgaacagctcttctgagacattggtcgcctctgagcctccccaaaccacaaaggagaag   60
 61 cctagcaagcccacctctcaagtcagatgggctcccattcgtggcatccctatcgagaga  120
121 agactgcagatgctggctgtctgcacatggatcagcatgatgttcattttggtgtetttg  180
181 tttttcttcatggccacctacaagttcatgtggcccattctgatcgcctacatcagcttt  240
241 ttgtacgtcgacaaagcccccgaatctggtggccgtagatttgaaagcgccagacactgg  300
301 gctctgtggagatatttcgctgcctacttccccgctcaactgatcaaggagcacgatttg  360
361 gaccccaagaacaattatgtctttggttaccaccccacggcattatctcttacggtgcc   420
421 cagctggcctttgctaccgaggctaccggctttagcgagaagttccccggtatcacaccc  480
481 agcttgctgacattgaacagcaacttccgtatccctttctaccgtgacgtgatcatggct  540
541 ttgggcatcgcttctgtcagccgtcgttcttgcgagaacattctgtctagcggcccggt   600
601 agatctatcgctatcgtcgtcggtggcgccgctgaaagcttgaacgccagacccggtacc  660
661 gctgatctggtgttgcgtaaacgtctgggcttcatccgtctggccatcaagcacggcgct  720
721 tctttggtcccgtcttcagcttcggtgagaacgaagtctacgaccagctggacaacgcc   780
781 aagggctctaaggtcttcatgtaccagaagaagatgcaagctatgctgggcttcacaatg  840
841 cccttgttccatgcccgtggcatcttcaactacgacgtcggcatcatcccttcagacac   900
901 cagatcaccaccgtcgtcggtaagcctatcccccgtccccgctttggaagaggggccagacc  960
961 gaacccacacaagagcagatcttgcaagtccagaagctgtacatcgacgagttgttcacc 1020
1021 atttataataagtacaaggacgtgtacgccaaggaccgtaagcaagaactgcgtatcacc 1080
1081 gattga                                                       1086
```

(2) Construction of a Recombinant Vector

The fragment of SEQ ID NO: 1 obtained by PCR was recovered and was ligated to a pMAT 2075 vector, the ligation product was transformed into an *Escherichia coli* Top10 competent cell, and the transformation product was coated with an LB plate containing penbritin of 100 mg/L (peptone: 10 g/L, yeast extract: 5 g/L, NaCl: 10 g/L, and agar: 1.5%). After overnight culture at 37° C., colonies were selected and were inoculated into an LB liquid culture medium (peptone: 10 g/L, yeast extract: 5 g/L, and NaCl: 10 g/L), plasmid was extracted after 8-10 h for sequence determination, and the plasmid with correct sequence was named pMAT2075-DGAT, as shown in FIG. 1.

(3) Preparation of *Mucor circinelloides* Protoplasm

Spores of the *Mucor circinelloides* M65 strain (*Mucor circinelloides* WJ11 of uracil defective type) were inoculated into a plate of a YPG culture medium (yeast extract: 3 g/L, peptone: 10 g/L, glucose: 20 g/L, leucine: 20 µg/mL, uracil: 200 µg/mL, pH 4.5) to culture at 28° C. for 1 day. Monoclonal hyphae were planted on the plate of the YPG culture medium, and the spores could grow well after being cultured at 28° C. for 3-4 days. the plates where the spores grown well were taken, 5-6 mL of YPG culture medium was added to each plate, the spores were scraped with a sterilized coating rod, spore suspension liquid was collected into a sterilized 50 mL centrifugal tube, calculation was calculated by a hemocytometer, and the concentration of the spores was adjusted to $1 \times 10^7$ pieces/mL by the YPG with pH 4.5. 12.5 mL of the above spore suspension liquid was put into a sterilized 250 mL conical flask, and the conical flask was place in a refrigerator at 4° C. overnight to make the spores fully absorb water and swell. The conical flask was placed on a table concentrator under the conditions of 30° C. and 250 rpm for culture until the spores germinated. After centrifugation at 1100 rpm, the above material was washed with 5 mL of PS buffer solution with pH 6.5 [18.22 g of sorbitol and 20 mL of PBS buffer solution (NaCl: 137 mM; KCl: 2.7 mM; $Na_2HPO_4$: 10 mM; and $KH_2PO_4$: 2 mM)] for twice to wash off the culture medium. The above material was resuspended in a 5 mL of PS buffer solution, lyase with the final concentration being 4 mg/mL and chitosanase of 0.06 U/ml were added, and then the material was placed in a table concentration under the conditions of 30° C. and 60 rpm to perform incubation for 90 min to remove cell walls. After centrifugation at 100×g, the above material was washed with 0.5 M 4° C. precooled sorbitol solution for twice, 800 µL of 0.5 M sorbitol was added to gently blow, suck and resuspend the precipitate to obtain protoplasts which were sub-packaged into 100 µL/tube for future use.

(4) Construction of a recombinant strain Mc-DGAT

100 µL of the prepared *Mucor circinelloides* protoplasts and 1 µg of recombinant plasmid pMAT2075-DGAT were mixed uniformly for electric shock transformation, the mixture was added into 1 mL of precooled YPGS (sorbitol: 0.5 mol/L; yeast extract: 3 g/L; peptone: 10 g/L; and glucose: 20 g/L) at once after electric shock to perform incubation for 1 h under the conditions of 26° C. and 100 rpm, the YPGS was removed through centrifugation at 100×g, and after the product was resuspended by YNBS [sorbitol: 91.1 g/L; glutamic acid: 1.5 g/L; $(NH_4)_2SO_4$: 1.5 g/L; yeast extract: 0.5 g/L; glucose: 10 g/L; and pH was adjusted to 4.5, and thiamine and niacin were added after sterilization until the final concentration is 1 µg/mL], an MMC culture medium [casamino acid: 10 g/L; yeast extract: 0.5 g/L; glucose: 20 g/L; agar: 15 g/L; and the pH was adjusted to 3.2, and thiamine and niacin were added after sterilization until the final concentration is 1 µg/mL] was coated with the product uniformly for lucifugal culture at 28° C. for 3-4 days. Single-colony hyphae grown on eight plates were randomly selected and put on a new MMC plate to culture 28° C. for 2-3 days to collect spores, about 200-300 spores were inoculated into the MMC and the uracil-containing MMC plate respectively to culture 28° C. for 2-3 days and the counting was conducted, and the above screening step was repeated until the number of the spores growing in the two plates was basically the same, indicating that a stable genetic transformant was obtained. After the stable genetic transformant hyphae were cultured in the YPG culture medium plate at 30° C. for 5-7 days, spores were collected, the concentration of the spores was adjusted to $1 \times 10^7$ pieces/mL, and the spores were stored in a 30% glycerinum tube at −80° C. The non-de novo synthesized *Mucor circinelloides* recombinant strain Mc-DGAT with high lipid yield was finally obtained; and the strain transformed into the pMAT2075 vector that did not integrate the DGAT nucleotide sequence serves as a control train Mc2075.

The remaining thalluses cultivated by the table concentrator after coating were separated by vacuum filtration with a Buchner funnel, the genome DNA of the non-de novo synthesized *Mucor circinelloides* recombinant strain Mc-DGAT with high lipid yield was extracted (referring to the instruction of a plant rapid DNA extraction kit), and PCR verification was conducted by taking the DNA as a template and taking 2075-F and 2075-R as primers.

2075-F: 5'-CGAGAACATTCTGTCTAGCG-3' (SEQ ID NO: 4)

2075-R: 5'-CATACACGGCCCACATTATC-3' (SEQ ID NO: 5)

Figure 2:
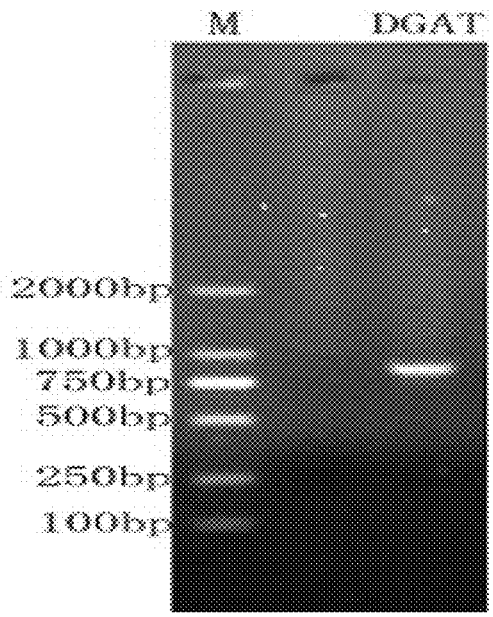
FIG. 2 is a PCR verification result of a *Mucor circinelloides* recombinant strain (M: standard protein molecular weight; DGAT: a plasmid fragment containing DGAT)

The reaction system and the amplification condition are as follows: pre-denaturation at 95° C. for 3 min, denaturation at 95° C. for 30 sec, annealing at 60° C. for 30 sec, extension at 72° C. for 2 min, 30 cycles, and compensative extension at 72° C. for 10 min. The PCR verification result is shown in FIG. 2. The fragment obtained by the non-de novo synthesized *Mucor circinelloides* recombinant strain Mc-DGAT with high lipid yield is 964 bp, indicating that the recombinant plasmid pMAT2075-DGAT has been successfully transformed into the *Mucor circinelloides*.

Embodiment 2

A method for producing lipid by a non-de novo synthesized *Mucor circinelloides* recombinant strain with high lipid yield through fermentation includes:

Seed fermentation liquid of the non-de novo synthesized *Mucor circinelloides* recombinant strain Mc-DGAT with high lipid yield was inoculated into a fermentation medium added with soybean oil as a carbon source according to the inoculation quantity of 10%; and during fermentation, a defoaming agent polypropylene glycol 2000 according to 2 mL/L was added, wherein the fermentation conditions are 28° C. and 600 rpm, the air inflow is v/v min$^{-1}$, and the pH is maintained to be 6.0. After fermentation, all the fermentation liquid samples were collected, vacuum filtration was conducted by a Buchner funnel, the fermentation liquid and thalluses were separated, the fermentation liquid was collected to store at −20° C. for future use, and the thalluses were washed with distilled water for three times and then were freeze-dried for future use.

The fermentation medium (1L) consists of:

40 g of glucose, 21.6 g of soybean oil, 1.5 g of $MgSO_4·7H_2O$, 100 μL of metal mother liquid, 2 g of ammonium tartrate, 7.0 g of $KH_2PO_4$, 2 g of $NaHPO_4$, 1.5 g of yeast extract, 0.1 g of $CaCl_2·2H_2O$ and the balance of water, wherein the metal mother liquid consists of: 8 g of $FeCl_3·6H_2O$, 1 g of $ZnSO_4·7H_2O$, 0.1 g of $CuSO_4·5H_2O$, 0.1 g of $Co(NO_3)_2·6H_2O$, 0.1 g of $MnSO_4·5H_2O$ and the balance of distilled water to prepare 100 mL.

When the soybean oil was added into the fermentation medium, emulsification treatment was conducted in advance, wherein the emulsification process is as follows: 1 wt % of tween 80 and a small amount of water (about 5-10 mL) were added into the soybean oil, homogenization was conducted by a homogenizer for 5 min under the condition of 8000 rpm, ultrasonic treatment was conducted for 5 min and then homogenization was conducted for 3 min.

Figure 3:
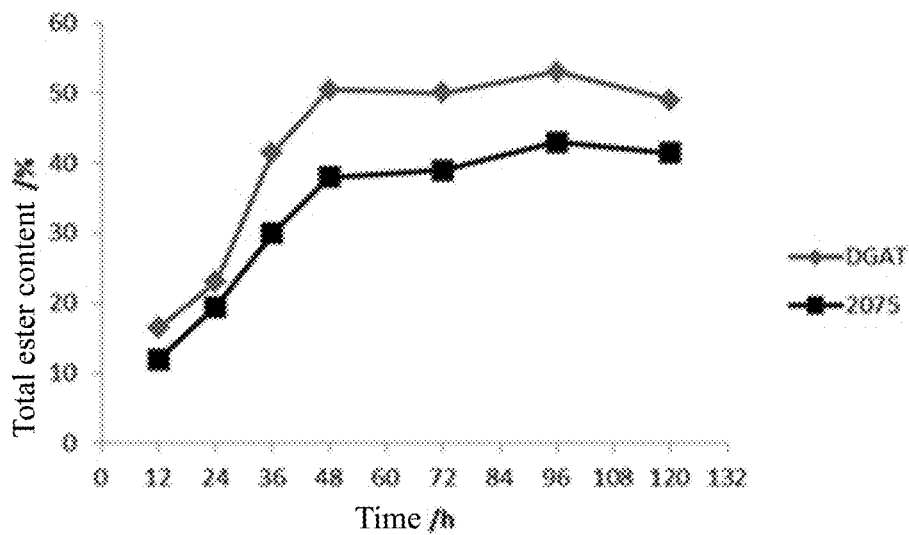
FIG. 3 is the content of total intracellular fat of a recombinant strain Mc-DGAT through fermentation culture and a control strain Mc2075.

Measurement of fermentation performance of a non-de novo synthesized *Mucor circinelloides* recombinant strain Mc-DGAT with high lipid yield (1) Measurement of content of fat produced by the non-de novo synthesized *Mucor circinelloides* recombinant strain Mc-DGAT with high lipid yield through fermentation Preparation of a to-be-measured sample: an optimized Kendrick culture medium was adopted in 1 L of fermentation tank, and soybean oil was added as a carbon source to culture the *Mucor circinelloides* recombinant strain Mc-DGAT. According to the oil production rule of the *Mucor circinelloides*, fermentation liquid was collected respectively at the 12 h, 24 h, 36 h, 48 h, 60 h, 72 h and 96 h during fermentation, and the fat content of the strain was measured by a method of double differences. The results are shown in Table 1 and FIG. 3. The intracellular fat content of the *Mucor circinelloides* recombinant strain Mc-DGAT with high lipid yield is increased compared with that of the control strain Mc2075.

TABLE 1

Content of intracellular fat of a recombinant strain Mc-DGAT through fermentation culture and a control strain Mc2075

| Strain | Fermentation Time (h) | | | | | | |
|---|---|---|---|---|---|---|---|
| | 12 | 24 | 36 | 48 | 60 | 72 | 96 |
| Mc-DGAT | 16.5 | 23 | 41.5 | 50.5 | 50 | 53 | 49 |
| Mc-DGAT | 12 | 19.5 | 30 | 38 | 39 | 41 | 40.5 |

(2) Measurement of content of fat acid produced by the non-de novo synthesized *Mucor circinelloides* recombinant strain Mc-DGAT with high lipid yield through fermentation Fermentation liquid was collected respectively at the 24 h, 36 h, 48 h, 60 h, 72 h and 96 h, 120 h during fermentation, and the content of the total fatty acids and the content of different types of fatty acids in the strain were measured by a gas phase. The results are shown in FIG. 4, FIG. 5 and FIG. 6.

Figure 4:
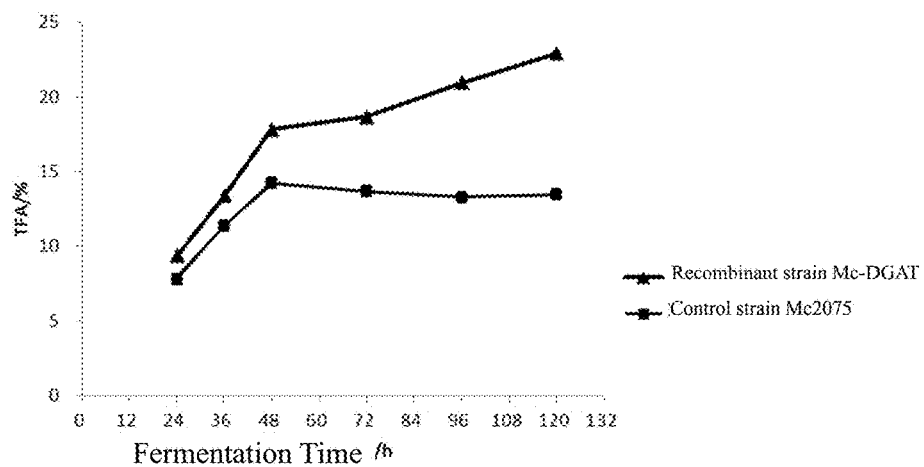
FIG. 4 is the content of total fatty acids produced by a non-de novo synthesized *Mucor circinelloides* recombinant strain Mc-DGAT with high lipid yield through fermentation.

It can be seen from FIG. 4 that the non-de novo synthesized *Mucor circinelloides* recombinant strain Mc-DGAT with high lipid yield shows a continuous increase trend with the fermentation time; and in the control strain Mc2075, the content of the total fatty acids reaches the highest at the 48 h of fermentation and then shows a basically stable trend.

Figure 5:
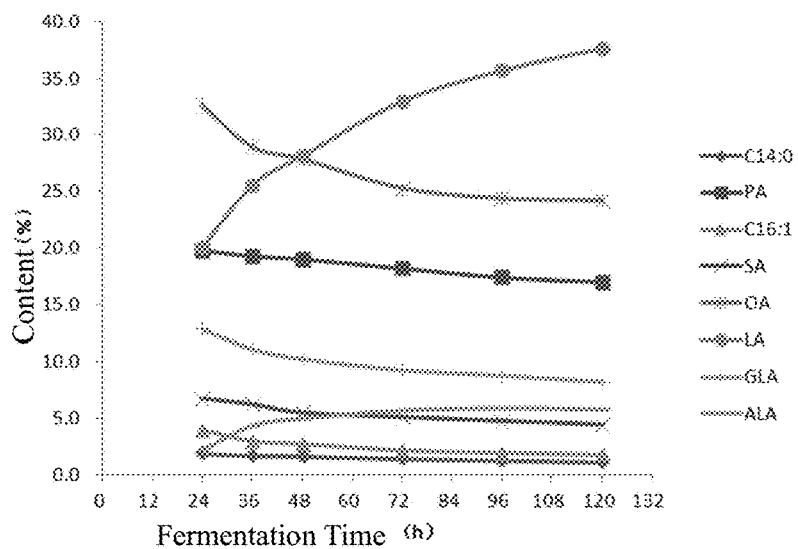
FIG. 5 is the content of different types of fatty acids fermented by a non-de novo synthesized *Mucor circinelloides* recombinant strain Mc-DGAT with high lipid yield.
Figure 6:
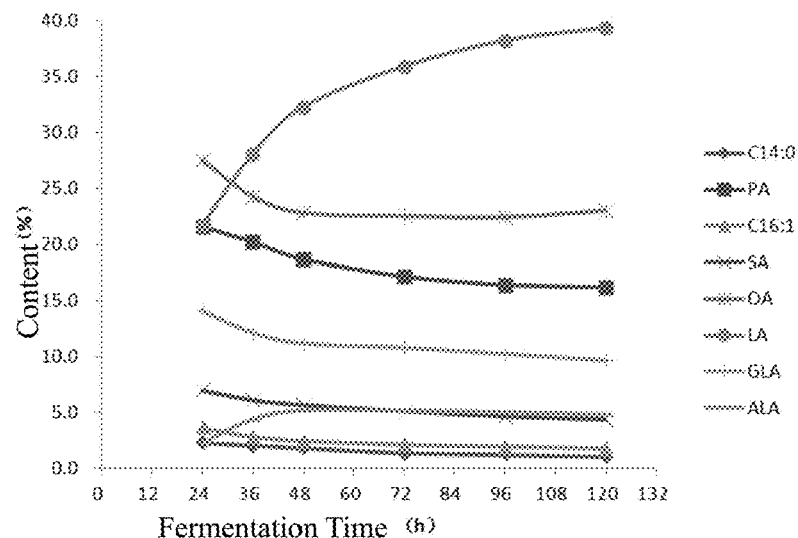
FIG. 6 is the content of different types of fatty acids fermented by a control strain Mc2075.

It can be seen from FIG. 5 and FIG. 6 that with the fermentation time, compared with the control strain Mc2705, the content of other six fatty acids except PA and OA of the non-de novo synthesized *Mucor circinelloides* recombinant strain Mc-DGAT with high lipid yield has little change; when the recombinant strain Mc-DGAT is used for fermentation, the PA content decreases slowly with the fermentation time, and the PA content of the control strain Mc2075 decreases rapidly at the half stage of fermentation; and the OA content of the recombinant strain Mc-DGAT is higher than the OA content of the control strain Mc2075.

The above description is only a preferred embodiment of the present invention, and is not intended to limit the present invention in other forms. Any person skilled in the art may change or modify the technical contents disclosed above into an equivalent embodiment with equivalent change. However, any simple amendment or equivalent change and modification of the above embodiments made according to the technical essence of the present invention without departing from the content of the technical solution of the present invention shall fall within the protection scope of the technical solution of the present invention.

What is claimed is:

1. A method for constructing a synthesized *Mucor circinelloides* recombinant strain, comprising:
   (a) inserting a polynucleotide encoding a diacylglycerol acyltransferase into a plasmid,
   (b) transforming a uracil defective *Mucor circinelloides* strain with the plasmid obtained in step (a), and
   (c) screening for clones that express the diacylglycerol acyltransferase and produce lipids, wherein the polynucleotide comprises SEQ ID NO: 1.

2. The method according to claim 1, wherein the uracil defective *Mucor circinelloides* is a variant of the *Mucor circinelloides* WJ11 strain that is uracil defective.

3. A *Mucor circinelloides* recombinant strain which has been deposited in the China General Microbiological Culture Collection Center (CGMCC) on Sep. 23, 2020 under deposit number CGMCC No. 20730.

4. A method for producing a lipid by fermentation of the *Mucor circinelloides* recombinant strain according to claim 3, wherein the method comprises culturing the *Mucor circinelloides* recombinant strain in a fermentation medium that comprises fat as a carbon source, and polypropylene glycol 2000 as a defoaming agent, wherein the fermentation conditions are 28° C. and 600 rpm, the air inflow is 1 v/v $min^{-1}$, and the pH is maintained at 6.0.

5. The method according to claim 4, wherein one liter of the fermentation medium consists of 40 g glucose, 21.6 g of fat, 1.5 g of $MgSO_4 \cdot 7\ H_2O$, 100 μL of metal mother liquid, 2 g of ammonium tartrate, 7.0 g of $KH_2PO_4$, 2 g of $NaHPO_4$, 1.5 g of yeast extract, 0.1 g of $CaCl_2 \cdot 2H_2O$ and water, and wherein 100 mL of the metal mother liquid consists of 8 g of $FeCl_3 \cdot 6H_2O$, 1 g $ZnSO_4 \cdot 7H_2O$, 0.1 g of $CuSO_4 \cdot 5H_2O$, 0.1 g of $Co(NO_3)_2 \cdot 6\ H_2O$, 0.1 g of $MnSO_4 \cdot 5\ H_2O$ and water.

6. The method according to claim 4, wherein the fat is soybean oil.

7. The method according to claim 4, wherein the fat is added after being emulsified, wherein the emulsification comprises (i) emulsifying the fat by adding 1 wt % of Tween 80 and a small amount of water into the fat to form a mixture, (ii) homogenizing the mixture of (i) for 5 minutes at 8000 rpm, (iii) applying ultrasound to the mixture for 5 minutes, and (iv) performing homogenization for 3 minutes.

* * * * *

SEQUENCE LISTING

<160> NUMBER OF SEQ ID NOS: 5

<210> SEQ ID NO 1
<211> LENGTH: 1086
<212> TYPE: DNA
<213> ORGANISM: Unknown
<220> FEATURE:
<223> OTHER INFORMATION: Diacylglycerol acyltransferase DGAT

<400> SEQUENCE: 1

```
atgaacagct cttctgagac attggtcgcc tctgagcctc cccaaaccac aaaggagaag      60
cctagcaagc ccacctctca agtcagatgg gctcccattc gtggcatccc tatcgagaga     120
agactgcaga tgctggctgt ctgcacatgg atcagcatga tgttcatttt ggtgtctttg     180
tttttcttca tggccaccta caagttcatg tggcccattc tgatcgccta catcagcttc     240
ttgtacgtcg acaaagcccc cgaatctggt ggccgtagat ttgaaagcgc cagacactgg     300
gctctgtgga gatatttcgc tgcctacttc cccgctcaac tgatcaagga gcacgatttg     360
gaccccaaga caattatgt ctttggttac cacccccacg gcattatctc ttacggtgcc     420
cagctggcct ttgctaccga ggctaccggc tttagcgaga gttccccgg tatcacaccc     480 agcttgctga cattgaacag caacttccgt atcccttct accgtgacgt gatcatggct     540
ttgggcatcg cttctgtcag ccgtcgttct tgcgagaaca ttctgtctag cggcccggt     600 agatctatcg ctatcgtcgt cggtggcgcc gctgaaagct tgaacgccag acccggtacc     660
gctgatctgg tgttgcgtaa acgtctgggc ttcatccgtc tggccatcaa gcacggcgct     720
tctttggtcc ccgtcttcag cttcggtgag aacgaagtct acgaccagct ggacaacgcc     780
aagggctcta aggtcttcat gtaccagaag aagatgcaag ctatgctggg cttcacaatg     840
cccttgttcc atgcccgtgg catcttcaac tacgacgtcg gcatcatccc cttcagacac     900
cagatcacca ccgtcgtcgg taagcctatc cccgtccccg cttggaaga gggccagacc     960 gaacccacac aagagcagat cttgcaagtc cagaagctgt acatcgacga gttgttcacc    1020
atttataata gtacaagga cgtgtacgcc aaggaccgta gcaagaact gcgtatcacc    1080 gattga                                                              1086
```

<210> SEQ ID NO 2
<211> LENGTH: 30
<212> TYPE: DNA
<213> ORGANISM: Unknown
<220> FEATURE:
<223> OTHER INFORMATION: Primer DGAT-F

<400> SEQUENCE: 2

```
agtcgctagc atgaacagct cttctgagac                                       30
```

<210> SEQ ID NO 3
<211> LENGTH: 30
<212> TYPE: DNA
<213> ORGANISM: Unknown
<220> FEATURE:
<223> OTHER INFORMATION: Primer DGAT-R

<400> SEQUENCE: 3

```
agtcgctagc tcaatcggtg atacgcagtt                                       30
```

<210> SEQ ID NO 4
<211> LENGTH: 20
<212> TYPE: DNA
<213> ORGANISM: Unknown

```
<220> FEATURE:
<223> OTHER INFORMATION: Primer 2075-F

<400> SEQUENCE: 4
cgagaacatt ctgtctagcg                                           20

<210> SEQ ID NO 5
<211> LENGTH: 20
<212> TYPE: DNA
<213> ORGANISM: Unknown
<220> FEATURE:
<223> OTHER INFORMATION: Primer 2075-R

<400> SEQUENCE: 5
catacacggc ccacattatc                                           20
```